(12) United States Patent
Neal

(10) Patent No.: US 10,987,495 B2
(45) Date of Patent: Apr. 27, 2021

(54) INFLATABLE MEDICAL BALLOON WITH VARIABLE PROFILE

(71) Applicant: C.R. Bard, Inc., Tempe, AZ (US)

(72) Inventor: Scott Neal, Tempe, AZ (US)

(73) Assignee: C.R. BARD, INC., Tempe, AZ (US)

( * ) Notice: Subject to any disclaimer, the term of this patent is extended or adjusted under 35 U.S.C. 154(b) by 628 days.

(21) Appl. No.: 15/415,226

(22) Filed: Jan. 25, 2017

(65) Prior Publication Data
US 2018/0207408 A1 Jul. 26, 2018

(51) Int. Cl.
*A61M 25/00* (2006.01)
*A61M 25/10* (2013.01)
*A61B 17/00* (2006.01)

(52) U.S. Cl.
CPC ...... *A61M 25/104* (2013.01); *A61M 25/0026* (2013.01); *A61M 25/1011* (2013.01); *A61B 17/00* (2013.01); *A61B 2017/00783* (2013.01); *A61M 2025/1013* (2013.01); *A61M 2025/1072* (2013.01); *A61M 2025/1084* (2013.01); *A61M 2025/1086* (2013.01)

(58) Field of Classification Search
CPC ........ A61M 25/104; A61M 2025/1072; A61M 2025/1086; A61M 2025/1068; A61M 2025/1059; A61B 2017/00783; A61B 17/12118; A61F 2/95; A61F 2/958
See application file for complete search history.

(56) References Cited

U.S. PATENT DOCUMENTS

| 4,364,392 | A |   | 12/1982 | Strother et al. |             |
|-----------|---|---|---------|-----------------|-------------|
| 4,787,388 | A | * | 11/1988 | Hofmann         | A61M 25/1002 |
|           |   |   |         |                 | 604/913      |
| 5,103,817 | A | * | 4/1992  | Reisdorf        | A61M 16/0436 |
|           |   |   |         |                 | 128/207.14   |
| 5,308,323 | A | * | 5/1994  | Sogawa          | A61M 25/1011 |
|           |   |   |         |                 | 604/95.03    |
| 5,538,456 | A | * | 7/1996  | Liu             | A63H 33/30   |
|           |   |   |         |                 | 222/78       |
| 5,728,068 | A | * | 3/1998  | Leone           | A61F 2/958   |
|           |   |   |         |                 | 604/101.01   |

(Continued)

FOREIGN PATENT DOCUMENTS

| EP | 0411132 A1 | 2/1991 |
| EP | 2241284 A1 | 10/2010 |
| EP | 2734258 A1 | 5/2014 |

*Primary Examiner* — Manuel A Mendez
*Assistant Examiner* — Justin L Zamory
(74) *Attorney, Agent, or Firm* — King & Schickli, PLLC

(57) ABSTRACT

An apparatus for performing a medical procedure includes a balloon with a variable profile. The balloon includes at least one inflatable chamber occupied by a fluid, such as air, and solids, such as generally spherical balls. When the chamber is inflated, the solids are spaced apart as a result of their ability to move or flow, but when the chamber is evacuated, the solids become compacted and prevent it from fully collapsing. The balloon may have a plurality of inflatable chambers with solids in different arrangements to achieve different objectives during the medical procedure, such as for example stent deployment. For example, one chamber may be expanded while the other is restrained to alter the balloon geometry, such as for providing focused force or permitting perfusion.

22 Claims, 6 Drawing Sheets

(56) References Cited

U.S. PATENT DOCUMENTS

| | | | |
|---|---|---|---|
| 5,755,797 A * | 5/1998 | Baumgartner | A61F 2/441 |
| | | | 623/17.16 |
| 5,865,801 A | 2/1999 | Houser | |
| 6,010,480 A | 1/2000 | Abele et al. | |
| 6,022,359 A | 2/2000 | Frantzen | |
| 6,872,215 B2 | 3/2005 | Crocker et al. | |
| 8,465,481 B2 | 6/2013 | Mazzone et al. | |
| 8,469,925 B2 | 6/2013 | Rowe et al. | |
| 2001/0016725 A1 | 8/2001 | Valley | |
| 2004/0236365 A1 | 11/2004 | Cioanta | |
| 2007/0010845 A1 | 1/2007 | Gong | |
| 2007/0250104 A1 | 10/2007 | Condrea et al. | |
| 2008/0009792 A1 | 1/2008 | Henniges et al. | |
| 2009/0299327 A1 * | 12/2009 | Tilson | A61B 17/8816 |
| | | | 604/500 |
| 2010/0268191 A1 | 10/2010 | Trudel et al. | |
| 2013/0072792 A1 * | 3/2013 | Aggerholm | A61M 25/10 |
| | | | 600/435 |
| 2013/0123621 A1 | 5/2013 | Isham | |
| 2013/0345796 A1 | 12/2013 | Eidenschink | |
| 2014/0180242 A1 | 6/2014 | Tai | |

\* cited by examiner

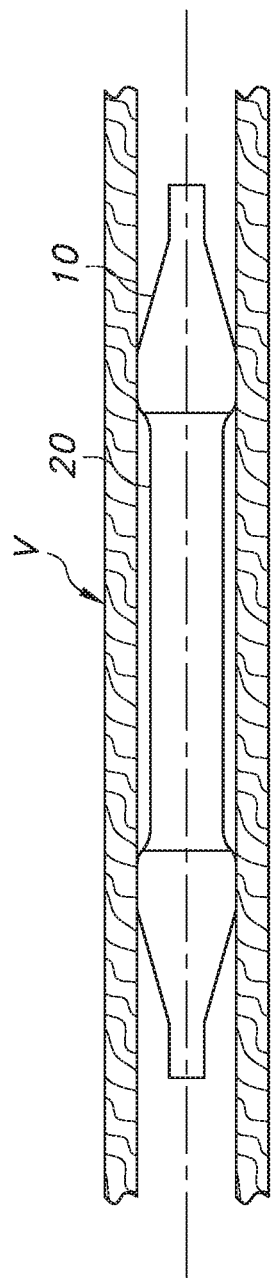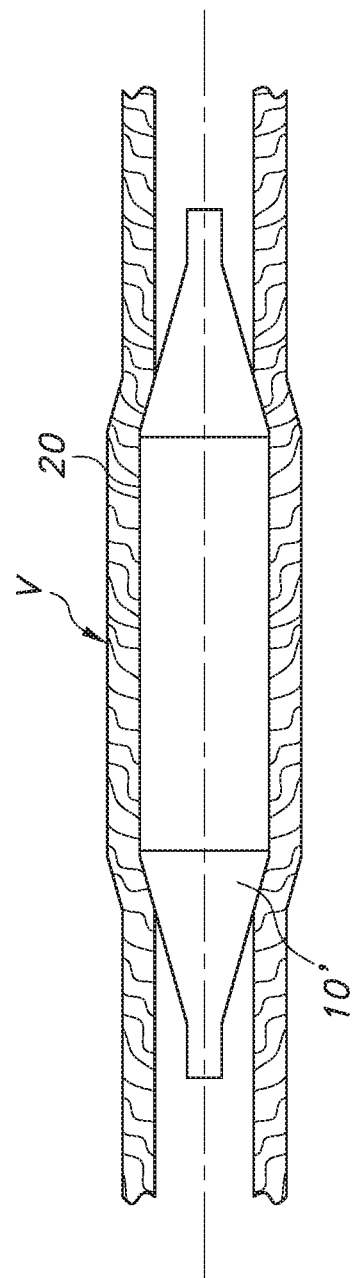

US 10,987,495 B2

INFLATABLE MEDICAL BALLOON WITH VARIABLE PROFILE

TECHNICAL FIELD

This document relates generally to the medical arts and, more particularly, to an inflatable medical balloon with a variable profile.

BACKGROUND

Inflatable balloons are commonly used in catheters for performing medical procedures, such as percutaneous transluminal angioplasty or valvuloplasty. Traditional balloons include a single hollow and expandable chamber that can inflated with a fluid to perform the desired procedure. As can be appreciated, the balloon when inflated has a fixed geometry or profile, which may limit its usefulness in performing procedures where a particular outcome, such as through the application of a targeted force, as but one example.

Accordingly, a need is identified for a medical balloon with a variable profile. The balloon would be relatively easy and inexpensive to manufacture using existing techniques, and would be readily adapted for use in connection with a variety of interventional procedures.

SUMMARY

Summarizing the disclosure, an apparatus for performing a medical procedure includes an inflatable balloon providing a variable profile as a result of the expansion state of one or more chambers with solids sealed therein. By selectively controlling the state of inflation, a variety of objectives may be achieved, including for example steering the balloon or providing for external perfusive flow as a result of the complex (e.g., non-circular) geometry achieved as a result.

In one disclosed embodiment, the balloon comprises a plurality of inflatable chambers, each with solids sealed therein. A shaft may also support the balloon. The shaft may include a lumen for communicating with each of the plurality of inflatable chambers, or one lumen may communicate with multiple chambers.

The plurality of inflatable chambers may, in one example, comprise a first inflatable chamber, a second inflatable chamber, and a third inflatable chamber positioned between the first and second inflatable chambers. The first inflatable chamber may be located at a proximal end portion of the balloon and the second inflatable chamber may be located at a distal end portion of the balloon. The first, second, and third inflatable chambers may be located in a single cross section of the balloon. The balloon may include at least four inflatable chambers, each with solids sealed therein, and possibly more or fewer such chambers.

The solids may comprise balls, which may be generally spherical or round in shape. The inflatable chamber may be at least partially bounded by an elastic material, which allows for the desired expansion and contraction to occur as a result of the evacuation and inflation of the chambers. The balloon may also include an inflatable chamber without solids, which may be partially bounded by one or more inflatable chambers with solids.

In accordance with a further aspect of the disclosure, an apparatus for performing a medical procedure is provided. The apparatus comprises a balloon with an inflatable chamber having a distal end portion and a proximal end portion. The apparatus further includes a first inflatable chamber at the distal end portion of the balloon, a second inflatable chamber at the proximal end portion of the balloon, and a third inflatable chamber between the first and second inflatable chambers.

In one embodiment, each of the first, second, and third inflatable chambers comprises solids sealed therein. The apparatus may further include a shaft supporting the balloon. The shaft may include a lumen for communicating with each one of the first, second, and third inflatable chambers. The apparatus may further include a stent at least partially overlying the third inflatable chamber. The balloon may include a first tapered end including the first inflatable chamber, a second tapered end including the second inflatable chamber, and an intermediate barrel portion including the third inflatable chamber.

According to still a further aspect of the disclosure, an apparatus for performing a medical procedure may be provided. The apparatus comprises a balloon having an expanded chamber and a restrained chamber in a single cross-section. The restrained chamber may include solids, and may also include a predetermined volume of air or be evacuated.

BRIEF DESCRIPTION OF THE DRAWING FIGURES

The accompanying drawing figures incorporated herein and forming a part of the specification, illustrate several aspects of an inflatable medical balloon with a variable profile and, together with the description, serve to explain certain principles thereof. In the drawing figures.

Figure 5B:
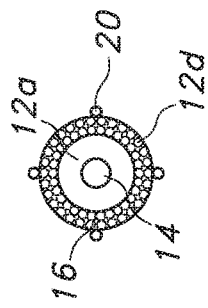
FIG. 5 is a perspective view illustrating a further embodiment of a variable profile balloon including a stent positioned along a restrained portion of the balloon and bounded by expanded end portions of the balloon.
Figure 5C:
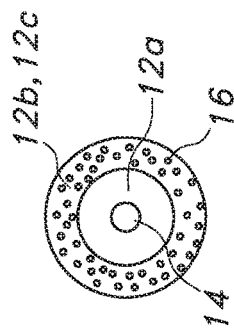
Figure 5D:
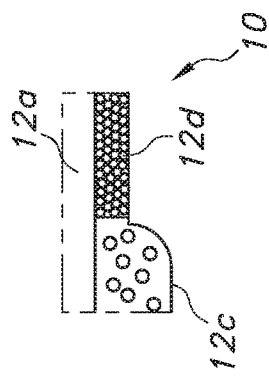
Figure 5:
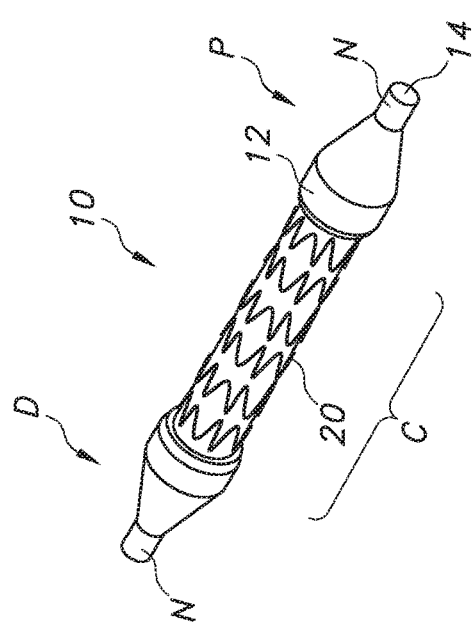
Figure 5A:
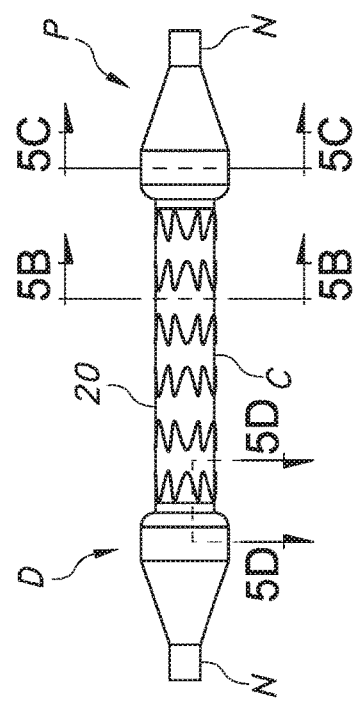
Figure 7:
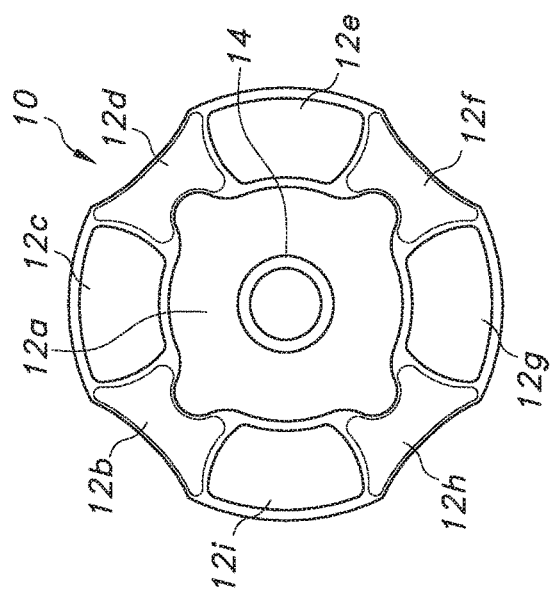
Figure 8:
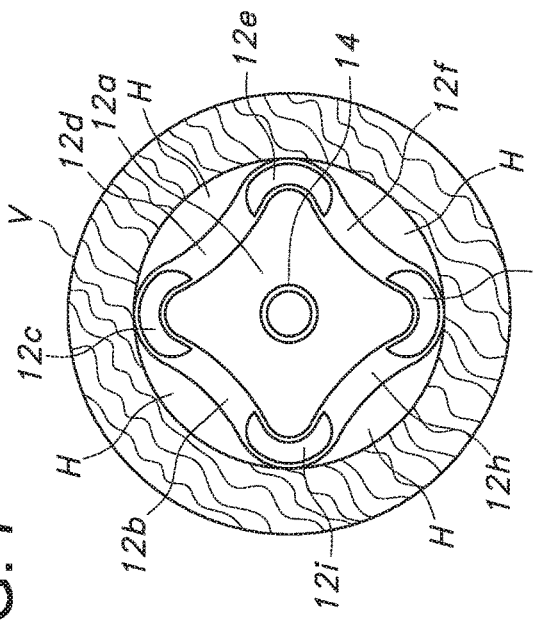

FIGS. 5B, 5C, and 5D are cross-sectional views taken along lines 5B-5B, 5C-5C, and 5D-5D of the side view of FIG. 5A;

FIGS. 6 and 6A illustrate the balloon of FIG. 5 in a partially and fully inflated condition, respectively; and FIGS. 7 and 8 are cross-sectional views of yet another embodiment of the balloon for possible use in performing a valvuloplasty procedure.

Reference will now be made in detail to the presently disclosed embodiments of the inventive aspects of the inflatable medical balloon with a variable profile, examples of which are illustrated in the accompanying drawing figures.

DETAILED DESCRIPTION

Figure 1A:
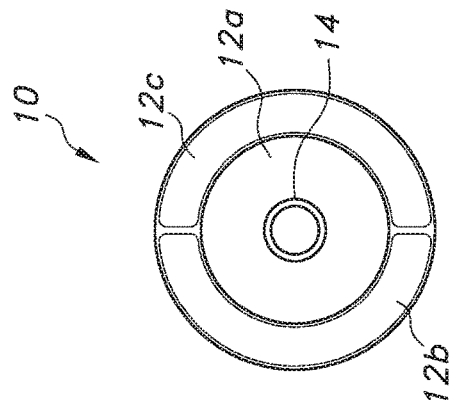
FIGS. 1A and 1C are cross-sectional views taken along line 1B-1B of the side view of FIG. 1B.
Figure 1C:
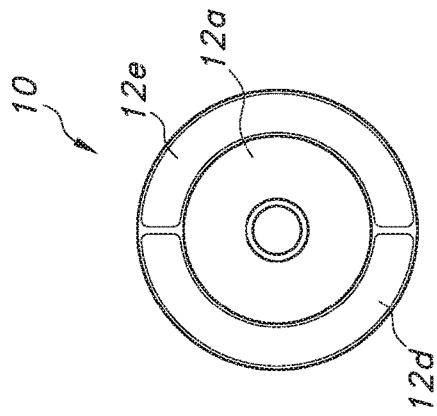
Figure 1:
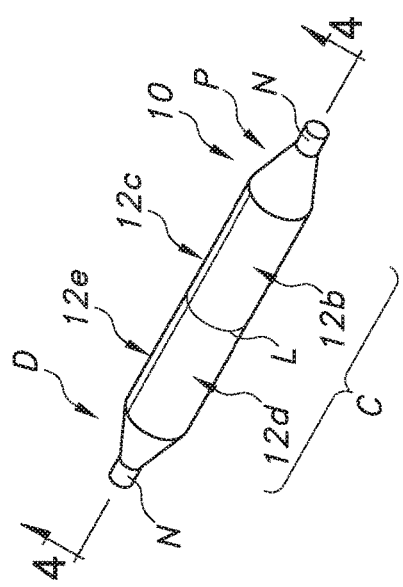
FIG. 1 is a perspective view of an inflatable medical balloon with a variable profile according to one aspect of the disclosure.
Figure 1B:
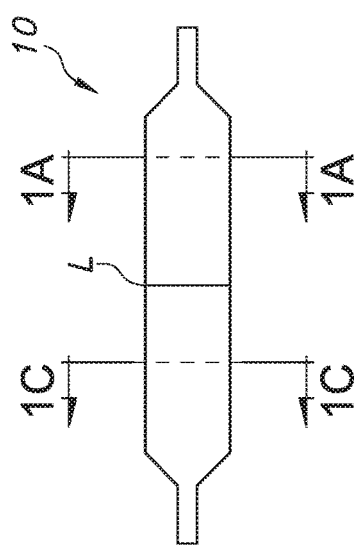
FIG. 1D is a partially cutaway cross-sectional view of the balloon of FIG. 1.
Figure 1D:
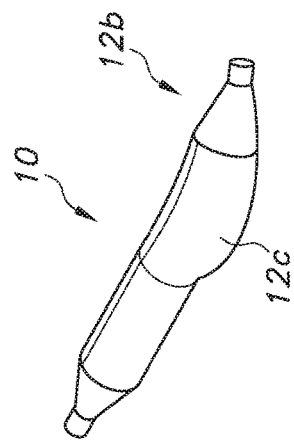

Reference is now made to FIGS. 1, 1A, 1B, 1C, and 1D, which illustrate one embodiment of a medical balloon 10 having a variable profile. As indicated, the balloon 10 includes a plurality of inflatable chambers 12, which may for example include at least one interior chamber 12a and at least one peripheral chamber 12b. As indicated in FIG. 1D, the walls 10a, 10b of the balloon 10 forming all or part of the chambers 12 may be formed of an elastic material, which thus allows the chambers to at least partially expand as a result of the application of gas or fluid (e.g. air or saline) pressure.

As indicated in FIG. 1A, the balloon 10 may be connected to and supported by a shaft 14. The balloon 10 may also include a proximal end portion P, which may be tapered to meet with the shaft at a neck N, a distal end portion D, which may be similarly tapered, and a central or intermediate portion C. The central or "barrel" portion C as it is sometimes called includes a working surface, which may carry a payload, such as a drug, stent, cutter, or the like.

In the illustrated embodiment, a single cross-section of the balloon 10 includes three inflatable chambers 12a, 12b, and 12c, as indicated by the cross-section shown in FIG. 1A. However, as can be appreciated from line of symmetry L in FIG. 1, the balloon 10 may include multiple peripheral chambers 12 in different parts, such as in both proximal and distal end portions P, D of the balloon 10, as can be understood from chambers 12d, 12e in FIG. 1C. While four peripheral chambers 12a, 12b, 12c, 12d are shown in FIG. 1, it should be appreciated that more or fewer may be provided (including as few as one such chamber). As can be further appreciated, the plurality of inflatable chambers 12 are also at least partially present in a longitudinal cross-section of the balloon 10 taken transverse to sections 1A-1A and 1C-1C.

Each of the plurality of chambers 12 may include solids that at least partially control the inflation state and thereby allow for the variable profile to be provided. For purposes of this disclosure, "solids" means unbounded materials capable of moving between a more compact or fixed condition in intimate contact (such as when the associated chamber is evacuated), to a more expanded or spaced apart condition (such as when the chamber is inflated). Thus, as one example shown in FIG. 1D, each of the inflatable chambers 12b, 12c along the periphery of the balloon 12 may be at least partially filled with a plurality of discrete balls 16. These balls 16 may be generally round or generally spherical in shape, but may take other forms (with a preference for those shapes that are free flowing when expanded, tightly compact when not, and otherwise will not harm the expandable (elastic) walls 10a, 10b forming the chambers 12). As discussed in more detail below, these balls 16 may be sealed within the chambers 12b, 12c in a manner that allows them to flow freely when a gas or fluid (such as air or saline) is present.

As indicated on the right hand side of FIG. 1D, the chamber 12 may be normally arranged such that a volume of fluid (air) is present between the inner and outer walls 10a, 10b of the balloon 10. This allows the balls 16 to separate and move freely in a random fashion about the chamber 12c. Interstitial spaces S result from the separation, thus forming an expanded chamber.

However, when the chamber 12 is deflated or evacuated, such as by drawing a vacuum on it or otherwise creating a negative pressure situation, as indicated by chamber 12' on the left hand side of FIG. 1D, the balls 16 become tightly compacted and organized by the walls 10a, 10b, such as into a regular or stacked arrangement. In such case, the balls 16 thereby limit the ability of the corresponding chamber 12c to reduce further in volume. In other words, the chamber 12b becomes restrained against further compaction as a result of the presence of solids (balls 16) therein.

Figure 2:
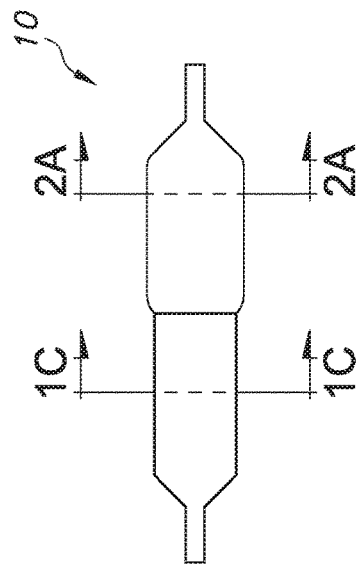
FIG. 2 illustrates the selective expansion and restraint of the chambers of the balloon.
Figure 2A:
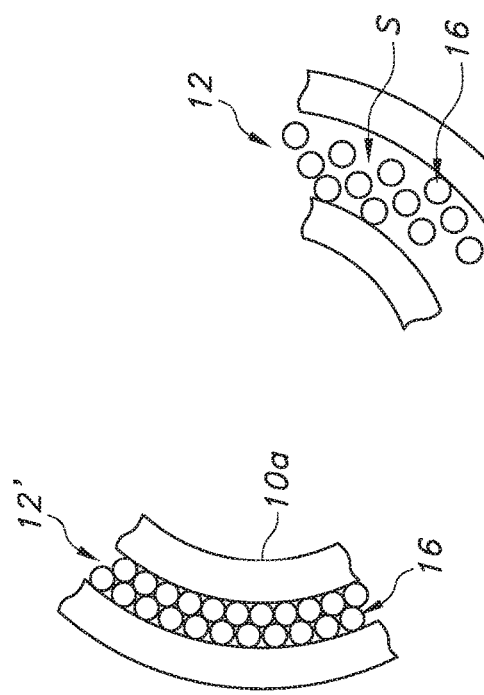
FIG. 2A is a cross-sectional view taken along line 2A-2A of the side view of FIG. 2B.
Figure 2B:
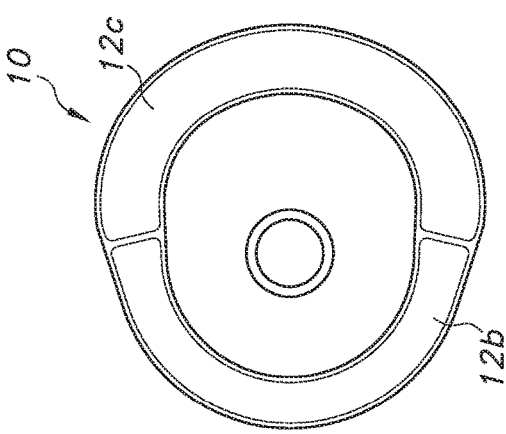

As can be appreciated, this ability to control the relative volume of the chamber or chambers 12 allows for the balloon 10 to be selectively manipulated to achieve a variable profile or geometry. For instance, using the above example and with further reference to FIGS. 2, 2A, and 2B, by expanding chamber 12a and chamber 12c, while restraining chamber 12b, the balloon 10 (which would normally assume a generally cylindrical shape on cross-section) is caused to assume a generally oblong cross-section, as shown in FIG. 2A. Thus, by selectively expanding or evacuating different chambers 12 of the balloon 10, a particular profile may be achieved to provide a desired treatment (such as by causing the balloon to expand more in one direction than another), or perhaps even to achieve steering capability by causing the balloon to assume a curved profile, as indicated in FIG. 2, which curved balloon 10 may thus alter the orientation of the connected shaft 14 and thus control the tracking direction of the guidewire lumen G (possibly for use in connection with subintimal reentry or for navigating tortuous vasculature).

Figure 3:
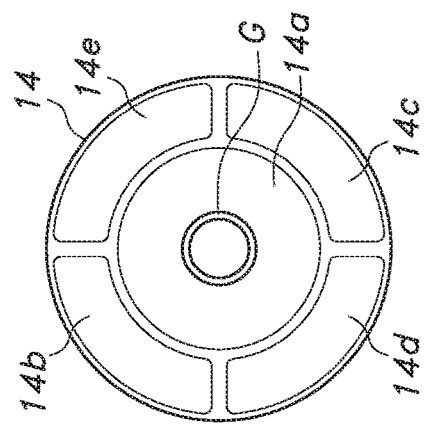
FIG. 3 is a cross-sectional view of one example of a multi-lumen shaft for the balloon.
Figure 4:
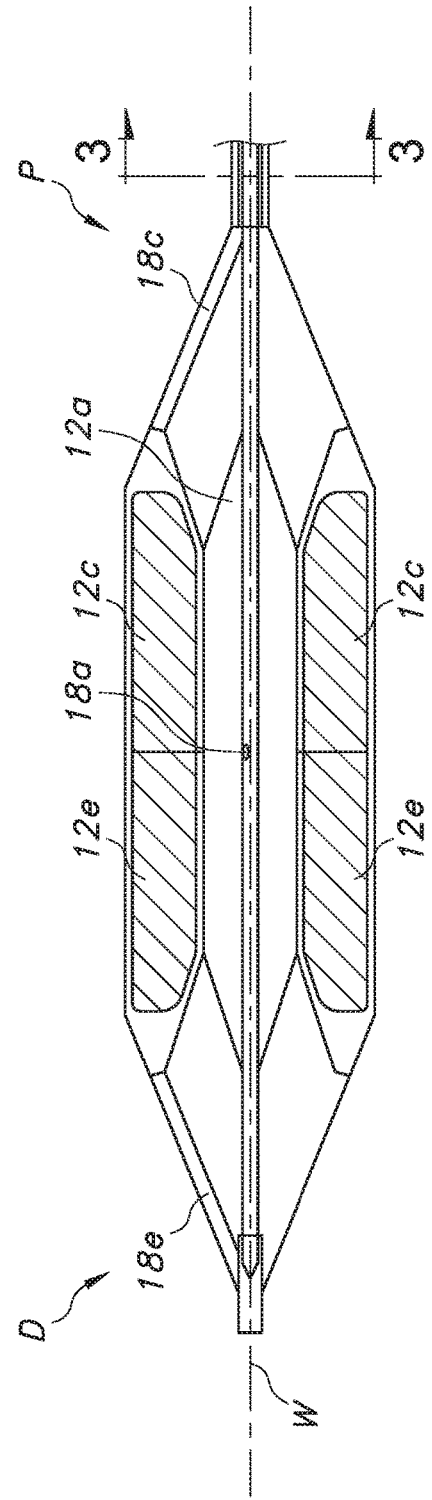
FIG. 4 is a partially cross-sectional side view of the balloon taken along line 4-4 of FIG. 1.

With reference to FIGS. 3 and 4, selective inflation or deflation of the chambers 12 may be achieved by providing the shaft 14 with corresponding lumens. These lumens may be discrete channels in a tube, as shown in FIG. 3. Alternatively, the lumens may comprise a group or bundle of distinct tubes associated with each chamber 12 (which again may be a single interior chamber 12a and a single peripheral chamber 12b, in which case only two lumens for inflation/evacuation would be required, one associated with each chamber 12a, 12b).

In the particular example illustrated, the shaft 14 includes an interior inflation lumen 14a corresponding to chamber 12a for inflating the balloon 10 generally, along with peripheral lumens 14b, 14c, 14d, 14e corresponding to chambers 12b, 12c, 12d, 12e. Each lumen 14a, 14b, 14c, 14d, 14e may be associated with a passage 18 (note passages 18c and 18e associated with the corresponding chambers 12c and 12e in FIG. 4, as well as passage 18a, which may simply be a port or hole in shaft 14 corresponding to lumen 14a for communicating fluid (such as saline or other liquid) to the interior chamber 12a). As indicated, each passage 18 may be in the form of a tube (and optionally covered by or within the balloon 10, as indicated by FIG. 1).

These passages 18 may be sized to allow for the passage of the selected inflation fluid, but not to allow the solids to pass. This ensures that the solids/balls 16 remain captured in the chambers 12. Alternatively, a filter (not shown) associated with the passage(s) 18 (or the inlet/outlet thereto) could be used for this purpose.

As indicated, the shaft 14 may also include a guidewire lumen G. This guidewire lumen G may extend distally of the balloon 10 for receiving a guidewire W. The arrangement may be an over-the-wire or rapid exchange configuration.

Referring now to FIGS. 5, 5A, 5B, 5C, and 5D, it can be appreciated that the variable profile balloon 10 may be used to deliver a payload, such as a stent 20, in an efficient and effective manner by using the selective inflation concepts described. In the illustrated example, the balloon 10 may include an interior chamber 12a, first and second chambers 12b, 12c surrounding the interior chamber 12a at the proximal end portion P and distal end portion D, and a third chamber 12d surrounding the interior chamber 12a along the center or barrel section C, which chamber includes an outer surface that supports the stent 20 (and thus is at least as long as the stent, and has a slightly smaller diameter). From the cross-sectional views of FIGS. 5B and 5C, it can be understood that the chambers 12b, 12c, 12d may be provided with solids, such as the balls 16. Alternatively, chambers 12b, 12c may simply be inflatable without including solids.

By restricting the third chamber 12d, such as through evacuation via a corresponding lumen and passage (not shown), while leaving the first and second chambers 12b, 12c expanded (or expanding them, if inflatable) and inflating the interior chamber 12a (if desired), the balloon 10 may have a single longitudinal cross-section including both restrained and unrestrained (expanded) portions, as indicated by FIG. 5D. This creates a partially reduced or "necked" configuration where the stent 20 is captured on the central or barrel portion C by the larger diameter walls of the balloon 10 created by the inflated end portions including the corresponding chambers. In this manner, the stent 20 is recessed within the margins of the smaller diameter portion of the balloon 10 for efficient delivery purposes relative to a treatment location in vessel V, as shown in FIG. 6.

When stent deployment is desired, the chambers 12b, 12c may be restrained, but remain uncollapsed in view of the presence of solids (balls 16). The third chamber 12d may be allowed to expand and the interior chamber 12a inflated to reverse the arrangement and create a larger diameter central or barrel portion C for expanding the stent 20 (note fully inflated balloon 10' in FIG. 6A). As a result of the controlled inflation, the phenomenon known as "watermelon-seeding" may be avoided. While a stent 20 is illustrated, it should be appreciated that the balloon 10 may carry other payloads, such as one or more pharmaceuticals/drugs, cutters, or the like.

With further reference to FIGS. 7 and 8, it can be appreciated that the selectively inflatable chambers 12 may be arranged in a circumferential manner in a single cross-section of the balloon 10. Thus, for instance, eight chambers 12b-12i may surround an interior chamber 12a. By selectively allowing certain of the chambers to remain inflated, such as chambers 12a, 12c, 12e, 12g, and 12i in FIG. 7, while restraining chambers 12b, 12d, 12f, and 12h, selected portions of the balloon 10 may be caused to deploy or retract, as shown. It can also be understood in this situation that a common lumen and passage may communicate with groups of the chambers occupied by solids, such that, for instance, chambers 12b, 12d, 12f, and 12h may be restrained by pulling a vacuum on a single lumen in communication therewith, while chambers 12c, 12e, 12g, and 12i are constantly inflated and need not be in fluid communication (but of course can be via a separate lumen).

As indicated in FIG. 8, the shape control afforded by the balloon 10 may be useful in connection with a valvuloplasty procedure in a vessel V associated with a valve (such as the aortic valve) to assist in "cracking" it to overcome any calcification. As can be appreciated, the selective inflation allows for the desired force profile to be provided, while allowing for channels H to remain so that blood flow to the heart is not occluded (and thus effectively providing a perfusion balloon).

Manufacture of the balloon 10 may be achieved using known techniques, such as for instance by way of extrusion to form a multi-chambered structure to serve as the balloon (which could be a preform that is expanded to a desired shape, such as by blow molding, as is well known). Other techniques, such as dip forming over a mandrel may be used. The balloon may comprise an elastic material (e.g. latex or similar), and may be formed by bonding components together (such as by solvent bonding or welding (ultrasonic or laser)). The particular dimensions and shape of the balloon 10 may vary depending on the desired application.

Once formed, the multi-chambered balloon 10 could be attached to the distal end portion of the shaft 14 such that the fluid passages or tubes (which may also be formed by extrusion) communicate with the chambers 12. The chambers 12 may then be loaded with the solids, such as balls 16, and a volume of air (which may be pre-determined to create a particular profile when inflated), such as from the ends. The chambers 12 may then be sealed accordingly to allow for selective inflation or evacuation via suitable device(s) in fluid communication with one or more of the lumens at a proximal end portion of the shaft 14.

Various methods of use are contemplated in light of the above-teachings. For instance, the balloon 10 may be used in connection with a situation involving a chronic total occlusion (CTO) by being directed subintimally and then reentering the vessel using the selective inflation and deflation of the chambers 12 to provide steering capabilities. A method for performing valvuloplasty may also involve selectively inflating one or more of the chambers, but restraining or evacuating others, while allowing for blood perfusion. A method of payload or stent deployment may also involve restraining a chamber to recess part of the balloon associated with the payload, while expanding other portions to provide a securing or retention function, and then expanding the balloon to deploy the payload.

In summary, a balloon 10 with a profile or geometry that may be varied by differential inflation is disclosed. The balloon 10 may include plural chambers 12 with solids, such as balls 16, enclosed in at least one elastic portion or wall. Deflating one or more of the chambers 12 may be achieved, such as by evacuation, which thus causes the corresponding portion to retract, but only to the extent of the volume of solids present. Other chambers 12 may remain expanded or be allowed to expand from a contracted state, in which case the solids simply disperse. As noted herein, the variable geometry or profile that results may be useful in a variety of medical procedures, such as stent or drug deployment in the vasculature, angioplasty, valvuloplasty, or others.

The foregoing description has been presented for purposes of illustration. It is not intended to be exhaustive or to limit the embodiments to the precise form disclosed. Obvious modifications and variations are possible in light of the above teachings. For instance, the balloon 10 may comprise only a single inflatable chamber 12b with solids that can be evacuated to be restrained (in other words, inflatable interior chamber 12a is considered optional). Likewise, the balloon 10 may be arranged differently than shown, such that one or more restrained chambers 12 with solids are positioned interior of an inflatable chamber 12a without solids. While elastic materials are desirable for forming balloon walls 10a, 10b to allow for repeated expansion and contraction as a result of changes in the inflation state, it should also be appreciated that the materials used may be semi-elastic. All modifications and variations are within the scope of the appended claims when interpreted in accordance with the breadth to which they are fairly, legally and equitably entitled.

What is claimed:
1. An apparatus for performing a medical procedure, comprising:
   a balloon having a plurality of inflatable chambers; and
   solids sealed within each of the plurality of inflatable chambers.

2. The apparatus of claim 1, further including a shaft supporting the balloon, the shaft comprising a lumen for communicating with each of the plurality of inflatable chambers.

3. The apparatus of claim 1, wherein the plurality of inflatable chambers comprise:
- a first inflatable chamber;
- a second inflatable chamber; and
- a third inflatable chamber positioned between the first and second inflatable chambers.

4. The apparatus of claim 3, wherein the first inflatable chamber is at a proximal end portion of the balloon and the second inflatable chamber is at a distal end portion of the balloon.

5. The apparatus of claim 3, wherein the first, second, and third inflatable chambers are located in a single cross section of the balloon.

6. The apparatus of claim 1, wherein the balloon comprises at least four inflatable chambers, each with solids sealed therein.

7. The apparatus of claim 1, wherein the solids comprise balls.

8. The apparatus of claim 1, wherein at least one of the plurality of inflatable chambers is at least partially bounded by an elastic material.

9. The apparatus of claim 1, wherein the balloon includes an additional inflatable chamber without solids, which additional chamber without solids is not one of the plurality of chambers with solids.

10. The apparatus of claim 9, wherein the inflatable chamber without solids is at least partially bounded by one of the plurality of inflatable chambers with solids.

11. The apparatus of claim 9, wherein the inflatable chamber without solids is at least partially bounded by the plurality of inflatable chambers with solids.

12. An apparatus for performing a medical procedure, comprising:
- a balloon having a distal end portion and a proximal end portion;
- a first inflatable chamber at the distal end portion of the balloon;
- a second inflatable chamber at the proximal end portion of the balloon; and
- a third inflatable chamber between the first and second inflatable chambers;
- wherein at least one of the first, second, and third inflatable chambers comprises solids sealed therein.

13. The apparatus of claim 12, wherein each of the first, second, and third inflatable chambers comprises solids sealed therein.

14. The apparatus of claim 12, further including a shaft supporting the balloon, the shaft comprising a lumen for communicating with each one of the first, second, and third inflatable chambers.

15. The apparatus of claim 12, further including a stent at least partially overlying the third inflatable chamber.

16. The apparatus of claim 12, wherein the balloon includes a first tapered end including the first inflatable chamber, a second tapered end including the second inflatable chamber, and an intermediate barrel portion including the third inflatable chamber.

17. An apparatus for performing a medical procedure, comprising:
- an inflatable balloon having an expanded chamber and a restrained chamber in a single cross-section, wherein the restrained chamber includes solids.

18. The apparatus of claim 17, wherein the restrained chamber is evacuated.

19. An apparatus for performing a medical procedure, comprising:
- a balloon having at least four inflatable chambers; and
- solids sealed within each of the at least four inflatable chambers.

20. An apparatus for performing a medical procedure, comprising:
- a balloon having a plurality of inflatable chambers; and
- balls sealed within the at least one inflatable chamber of the plurality of inflatable chambers.

21. An apparatus for performing a medical procedure, comprising:
- a balloon having at least one inflatable chamber at least partially bounded by an elastic material; and
- solids sealed within the at least one inflatable chamber.

22. An apparatus for performing a medical procedure, comprising:
- a balloon having a first inflatable chamber having solids sealed therein and a second inflatable chamber without solids.

* * * * *